(12) United States Patent
Sartor

(10) Patent No.: US 8,460,289 B2
(45) Date of Patent: *Jun. 11, 2013

(54) ELECTRODE WITH ROTATABLY DEPLOYABLE SHEATH

(75) Inventor: Joe Don Sartor, Longmont, CO (US)

(73) Assignee: Covidien AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/355,762

(22) Filed: Jan. 23, 2012

(65) Prior Publication Data

US 2012/0123412 A1 May 17, 2012

Related U.S. Application Data

(63) Continuation of application No. 12/363,322, filed on Jan. 30, 2009, now Pat. No. 8,100,902, which is a continuation of application No. 11/168,901, filed on Jun. 28, 2005, now Pat. No. 7,500,974.

(51) Int. Cl.
*A61B 18/14* (2006.01)

(52) U.S. Cl.
USPC .............................................. 606/45; 606/49

(58) Field of Classification Search
USPC .................................................... 606/45, 49
See application file for complete search history.

(56) References Cited

U.S. PATENT DOCUMENTS

| | | | |
|---|---|---|---|
| 2,031,682 A | 2/1936 | Charles et al. | |
| 2,102,270 A | 12/1937 | Hyams | |
| 2,964,796 A | 12/1960 | Press | |
| 2,993,178 A | 7/1961 | Burger | |
| 3,058,470 A | 10/1962 | Seeliger et al. | |
| 3,219,029 A | 11/1965 | Richards et al. | |
| 3,421,509 A | 1/1969 | Fiore | |
| 3,460,539 A | 8/1969 | Anhalt, Sr. | |
| 3,494,363 A | 2/1970 | Jackson | |
| 3,565,078 A | 2/1971 | Vailliancort et al. | |
| 3,648,001 A | 3/1972 | Anderson et al. | |
| 3,675,655 A | 7/1972 | Sittner | |
| 3,699,967 A | 10/1972 | Anderson | |

(Continued)

FOREIGN PATENT DOCUMENTS

| DE | 24 29 021 | 1/1976 |
|---|---|---|
| DE | 24 60 481 | 6/1976 |

(Continued)

OTHER PUBLICATIONS

International Search Report EP-04015980 dated Sep. 30, 2004.

(Continued)

*Primary Examiner* — Lee S Cohen

(57) ABSTRACT

A sheath system for selectively covering a distal end of an electrocautery blade is provided. The sheath system includes a hub having a body portion defining a lumen therethrough and a sheath having a body portion defining a lumen therethrough. The lumen of the sheath is configured and dimensioned to operatively receive an electrocautery blade therein. The sheath is translatably associated with the hub such that rotation of the hub in a first direction results in axial movement of the sheath in a first direction to expose a distal end of the electrocautery blade and rotation of the hub in a second direction, opposite to the first direction, results in axial movement of the sheath in a second direction to cover the distal end of the electrocautery blade. The hub and the sheath may be concentric with one another.

20 Claims, 7 Drawing Sheets

U.S. PATENT DOCUMENTS

| | | |
|---|---|---|
| 3,720,896 A | 3/1973 | Beierlein |
| 3,801,766 A | 4/1974 | Morrison, Jr. |
| 3,801,800 A | 4/1974 | Newton |
| 3,825,004 A | 7/1974 | Durden, III |
| 3,828,780 A | 8/1974 | Morrison, Jr. |
| 3,853,127 A | 12/1974 | Spademan |
| 3,875,945 A | 4/1975 | Friedman |
| 3,902,494 A | 9/1975 | Haberlen et al. |
| 3,906,955 A | 9/1975 | Roberts |
| 3,907,310 A | 9/1975 | Dufour |
| 3,911,241 A | 10/1975 | Jarrard |
| 3,967,084 A | 6/1976 | Pounds |
| 3,974,833 A | 8/1976 | Durden, III |
| 3,994,287 A | 11/1976 | Turp et al. |
| 4,000,739 A | 1/1977 | Stevens |
| 4,014,343 A | 3/1977 | Esty |
| 4,032,738 A | 6/1977 | Esty et al. |
| 4,034,761 A | 7/1977 | Prater et al. |
| 4,038,984 A | 8/1977 | Sittner |
| 4,112,932 A | 9/1978 | Chiulli |
| 4,112,950 A | 9/1978 | Pike |
| D253,247 S | 10/1979 | Gill |
| 4,173,350 A | 11/1979 | Sieghartner |
| 4,177,814 A | 12/1979 | Knepshield et al. |
| 4,177,997 A | 12/1979 | Cartwright |
| 4,232,676 A | 11/1980 | Herczog |
| 4,240,335 A | 12/1980 | Stucka et al. |
| 4,240,411 A | 12/1980 | Hosono |
| 4,311,315 A | 1/1982 | Kronenberg |
| 4,314,559 A | 2/1982 | Allen |
| 4,334,688 A | 6/1982 | Spargo et al. |
| 4,338,689 A | 7/1982 | Zieg |
| 4,386,756 A | 6/1983 | Muchow |
| 4,387,879 A | 6/1983 | Tauschinski |
| 4,427,006 A | 1/1984 | Nottke |
| 4,430,081 A | 2/1984 | Timmermans |
| 4,443,935 A | 4/1984 | Zamba et al. |
| 4,447,237 A | 5/1984 | Frisch et al. |
| 4,459,443 A | 7/1984 | Lewandowski |
| 4,463,234 A | 7/1984 | Bennewitz |
| 4,463,759 A | 8/1984 | Garito et al. |
| 4,464,178 A | 8/1984 | Dalton |
| 4,492,231 A | 1/1985 | Auth |
| 4,492,832 A | 1/1985 | Taylor |
| 4,545,375 A | 10/1985 | Cline |
| 4,553,760 A | 11/1985 | Reed et al. |
| 4,562,838 A | 1/1986 | Walker |
| 4,588,195 A | 5/1986 | Antonini et al. |
| 4,589,411 A | 5/1986 | Friedman |
| 4,593,691 A | 6/1986 | Lindstrom et al. |
| 4,595,809 A | 6/1986 | Pool |
| 4,601,710 A | 7/1986 | Moll |
| 4,606,342 A | 8/1986 | Zamba et al. |
| 4,619,258 A | 10/1986 | Pool |
| 4,620,548 A | 11/1986 | Hasselbrack |
| 4,625,723 A | 12/1986 | Altnether et al. |
| 4,626,245 A | 12/1986 | Weinstein |
| 4,640,279 A | 2/1987 | Beard |
| 4,641,842 A | 2/1987 | Kataoka |
| 4,642,128 A | 2/1987 | Solorzano |
| 4,654,030 A | 3/1987 | Moll et al. |
| 4,655,215 A | 4/1987 | Pike |
| 4,655,752 A | 4/1987 | Honkanen et al. |
| 4,657,016 A | 4/1987 | Garito et al. |
| 4,673,393 A | 6/1987 | Suzuki et al. |
| 4,683,884 A | 8/1987 | Hatfield et al. |
| 4,688,569 A | 8/1987 | Rabinowitz |
| 4,701,193 A | 10/1987 | Robertson et al. |
| 4,705,511 A | 11/1987 | Kocak |
| 4,712,544 A | 12/1987 | Ensslin |
| 4,715,360 A | 12/1987 | Akui et al. |
| 4,723,550 A | 2/1988 | Bales et al. |
| 4,735,603 A | 4/1988 | Goodson et al. |
| 4,754,754 A | 7/1988 | Garito et al. |
| 4,758,225 A | 7/1988 | Cox et al. |
| 4,785,807 A | 11/1988 | Blanch |
| 4,788,977 A | 12/1988 | Farin et al. |
| 4,790,312 A * | 12/1988 | Capuano et al. .............. 606/171 |
| 4,794,215 A | 12/1988 | Sawada et al. |
| 4,796,623 A | 1/1989 | Krasner et al. |
| 4,803,323 A | 2/1989 | Bauer et al. |
| 4,811,733 A | 3/1989 | Borsanyi et al. |
| 4,827,911 A | 5/1989 | Broadwin et al. |
| 4,827,927 A | 5/1989 | Newton |
| D301,739 S | 6/1989 | Turner et al. |
| 4,842,591 A | 6/1989 | Luther |
| 4,844,483 A | 7/1989 | Iijima et al. |
| 4,844,484 A | 7/1989 | Antonini et al. |
| 4,846,790 A | 7/1989 | Hornlein et al. |
| 4,850,353 A | 7/1989 | Stasz et al. |
| 4,857,062 A | 8/1989 | Russell |
| 4,860,745 A | 8/1989 | Farin et al. |
| 4,862,889 A | 9/1989 | Feucht |
| 4,862,890 A | 9/1989 | Stasz et al. |
| 4,869,715 A | 9/1989 | Sherburne |
| 4,869,717 A | 9/1989 | Adair |
| 4,872,454 A | 10/1989 | DeOliveira et al. |
| 4,874,378 A | 10/1989 | Hillstead |
| 4,876,110 A | 10/1989 | Blanch |
| 4,886,060 A | 12/1989 | Wiksell |
| 4,889,349 A | 12/1989 | Muller |
| 4,901,719 A | 2/1990 | Trenconsky et al. |
| 4,903,696 A | 2/1990 | Stasz et al. |
| 4,909,249 A | 3/1990 | Akkas et al. |
| 4,909,798 A | 3/1990 | Fleischhacker et al. |
| 4,911,159 A | 3/1990 | Johnson et al. |
| 4,916,275 A | 4/1990 | Almond |
| 4,917,668 A | 4/1990 | Haindl |
| 4,919,129 A | 4/1990 | Weber, Jr. et al. |
| 4,921,476 A | 5/1990 | Wuchinich |
| 4,922,903 A | 5/1990 | Welch et al. |
| 4,929,235 A | 5/1990 | Merry et al. |
| 4,931,047 A | 6/1990 | Broadwin et al. |
| 4,932,633 A | 6/1990 | Johnson et al. |
| 4,943,280 A | 7/1990 | Lander |
| 4,949,734 A | 8/1990 | Bernstein |
| 4,960,412 A | 10/1990 | Fink |
| 4,966,588 A | 10/1990 | Rayman et al. |
| 4,969,885 A | 11/1990 | Farin |
| 4,986,839 A | 1/1991 | Wertz et al. |
| 4,988,334 A | 1/1991 | Hornlein et al. |
| 4,998,740 A | 3/1991 | Tellier |
| 5,000,745 A | 3/1991 | Guest et al. |
| 5,000,754 A | 3/1991 | DeOliveira et al. |
| 5,002,557 A | 3/1991 | Hasson |
| 5,011,483 A | 4/1991 | Sleister |
| 5,013,312 A | 5/1991 | Parins et al. |
| 5,015,000 A | 5/1991 | Perini |
| 5,015,227 A | 5/1991 | Broadwin et al. |
| 5,026,085 A | 6/1991 | Ducote |
| 5,026,368 A | 6/1991 | Adair |
| 5,035,695 A | 7/1991 | Weber, Jr. et al. |
| 5,035,696 A | 7/1991 | Rydell |
| 5,038,756 A | 8/1991 | Kepley |
| 5,041,095 A | 8/1991 | Littrell |
| 5,046,506 A | 9/1991 | Singer |
| 5,053,014 A | 10/1991 | Van Heugten |
| 5,053,016 A | 10/1991 | Lander |
| 5,055,100 A | 10/1991 | Olsen |
| 5,071,418 A | 12/1991 | Rosenbaum |
| 5,073,169 A | 12/1991 | Raiken |
| 5,074,863 A | 12/1991 | Dines |
| 5,076,276 A | 12/1991 | Sakurai et al. |
| 5,085,657 A | 2/1992 | Ben-Simhon |
| 5,088,997 A | 2/1992 | Delahuerga et al. |
| 5,098,430 A | 3/1992 | Fleenor |
| 5,100,402 A | 3/1992 | Fan |
| 5,104,383 A | 4/1992 | Shichman |
| 5,108,391 A | 4/1992 | Flachenecker et al. |
| 5,127,626 A | 7/1992 | Hilal et al. |
| 5,133,714 A | 7/1992 | Beane |
| 5,137,520 A | 8/1992 | Maxson et al. |
| 5,147,292 A | 9/1992 | Kullas et al. |
| D330,253 S | 10/1992 | Burek |
| 5,154,709 A | 10/1992 | Johnson |
| 5,160,334 A | 11/1992 | Billings et al. |
| 5,162,044 A | 11/1992 | Gahn et al. |

| | | | | | |
|---|---|---|---|---|---|
| 5,167,636 A | 12/1992 | Clement | 5,462,522 A | 10/1995 | Sakurai et al. |
| 5,167,659 A | 12/1992 | Ohtomo et al. | 5,468,240 A | 11/1995 | Gentelia et al. |
| 5,178,012 A | 1/1993 | Culp | 5,472,442 A | 12/1995 | Klicek |
| 5,178,605 A | 1/1993 | Imonti | 5,472,443 A | 12/1995 | Cordis et al. |
| 5,180,373 A | 1/1993 | Green et al. | 5,484,398 A | 1/1996 | Stoddard |
| 5,190,517 A | 3/1993 | Zieve et al. | 5,484,434 A | 1/1996 | Cartmell et al. |
| 5,192,267 A | 3/1993 | Shapira et al. | 5,486,162 A | 1/1996 | Brumbach |
| 5,195,959 A | 3/1993 | Smith | 5,496,280 A | 3/1996 | Vandenbroek et al. |
| 5,196,007 A | 3/1993 | Ellman et al. | 5,496,314 A | 3/1996 | Eggers |
| 5,197,955 A | 3/1993 | Stephens et al. | 5,498,654 A | 3/1996 | Shimasaki et al. |
| 5,197,962 A | 3/1993 | Sansom et al. | 5,514,098 A | 5/1996 | Pfoslgraf et al. |
| 5,199,944 A | 4/1993 | Cosmescu | 5,519,197 A | 5/1996 | Robinson et al. |
| 5,201,714 A | 4/1993 | Gentelia et al. | D370,731 S | 6/1996 | Corace et al. |
| 5,209,736 A | 5/1993 | Stephens et al. | 5,531,722 A | 7/1996 | Van Hale |
| 5,209,737 A | 5/1993 | Ritchart et al. | 5,545,142 A | 8/1996 | Stephens et al. |
| 5,217,457 A | 6/1993 | Delahuerga et al. | 5,549,604 A | 8/1996 | Sutcu et al. |
| 5,221,264 A | 6/1993 | Wilk et al. | 5,561,278 A | 10/1996 | Rutten |
| 5,224,944 A | 7/1993 | Elliott | 5,601,224 A | 2/1997 | Bishop et al. |
| 5,226,891 A | 7/1993 | Bushatz et al. | 5,609,573 A | 3/1997 | Sandock |
| 5,226,904 A | 7/1993 | Gentelia et al. | 5,626,575 A | 5/1997 | Crenner |
| 5,233,515 A | 8/1993 | Cosman | 5,630,417 A | 5/1997 | Petersen et al. |
| 5,234,428 A | 8/1993 | Kaufman | 5,630,426 A | 5/1997 | Eggers et al. |
| 5,234,429 A | 8/1993 | Goldhaber | 5,630,812 A | 5/1997 | Ellman et al. |
| 5,242,412 A | 9/1993 | Blake, III | 5,633,578 A | 5/1997 | Eggers et al. |
| 5,242,442 A | 9/1993 | Hirschfeld | 5,634,908 A | 6/1997 | Loomas |
| 5,244,462 A | 9/1993 | Delahuerga et al. | 5,634,911 A | 6/1997 | Hermann et al. |
| 5,246,440 A | 9/1993 | Van Noord | 5,634,912 A | 6/1997 | Injev |
| 5,254,082 A | 10/1993 | Takase | 5,634,935 A | 6/1997 | Taheri |
| 5,254,117 A | 10/1993 | Rigby et al. | 5,634,937 A | 6/1997 | Mollenauer et al. |
| 5,256,138 A | 10/1993 | Burek et al. | 5,643,256 A | 7/1997 | Urueta |
| 5,261,905 A | 11/1993 | Doresey, III | D384,148 S | 9/1997 | Monson |
| 5,261,906 A | 11/1993 | Pennino et al. | 5,662,647 A | 9/1997 | Crow et al. |
| 5,261,918 A | 11/1993 | Phillips et al. | 5,667,489 A | 9/1997 | Kraff et al. |
| 5,269,781 A | 12/1993 | Hewell, III | 5,669,907 A | 9/1997 | Platt, Jr. et al. |
| 5,290,304 A | 3/1994 | Storace | 5,674,219 A | 10/1997 | Monson et al. |
| 5,299,813 A | 4/1994 | McKenna | 5,685,858 A | 11/1997 | Kawand |
| 5,300,036 A | 4/1994 | Mueller et al. | 5,693,044 A | 12/1997 | Cosmescu |
| 5,300,087 A | 4/1994 | Knoepfler | 5,693,050 A | 12/1997 | Speiser |
| 5,304,763 A | 4/1994 | Ellman et al. | 5,693,052 A | 12/1997 | Weaver |
| 5,306,238 A | 4/1994 | Fleenor | 5,697,926 A | 12/1997 | Weaver |
| 5,308,336 A | 5/1994 | Hart et al. | 5,702,360 A | 12/1997 | Dieras et al. |
| 5,312,329 A | 5/1994 | Beaty et al. | 5,702,387 A | 12/1997 | Arts et al. |
| 5,312,400 A | 5/1994 | Bales et al. | 5,712,543 A | 1/1998 | Sjostrom |
| 5,312,401 A | 5/1994 | Newton et al. | 5,713,895 A | 2/1998 | Lontine et al. |
| 5,313,935 A | 5/1994 | Kortenbach et al. | 5,720,745 A | 2/1998 | Farin et al. |
| 5,318,516 A | 6/1994 | Cosmescu | D393,067 S | 3/1998 | Geary et al. |
| 5,318,565 A | 6/1994 | Kuriloff et al. | 5,749,869 A | 5/1998 | Lindenmeier et al. |
| 5,322,503 A | 6/1994 | Desai | 5,749,871 A | 5/1998 | Hood et al. |
| 5,324,270 A | 6/1994 | Kayan et al. | 5,765,418 A | 6/1998 | Rosenberg |
| 5,330,470 A | 7/1994 | Hagen | 5,776,092 A | 7/1998 | Farin et al. |
| 5,334,183 A | 8/1994 | Wuchinich | 5,788,688 A | 8/1998 | Bauer et al. |
| 5,342,315 A | 8/1994 | Rowe et al. | 5,792,139 A | 8/1998 | Chambers et al. |
| 5,342,356 A | 8/1994 | Ellman et al. | 5,797,907 A | 8/1998 | Clement |
| 5,348,555 A | 9/1994 | Zinnanti | 5,800,431 A | 9/1998 | Brown |
| 5,366,464 A | 11/1994 | Belknap | 5,827,228 A | 10/1998 | Rowe |
| 5,376,077 A | 12/1994 | Gomringer | 5,827,280 A | 10/1998 | Sandock et al. |
| 5,376,089 A | 12/1994 | Smith | 5,836,897 A | 11/1998 | Sakurai et al. |
| 5,380,320 A | 1/1995 | Morris | 5,836,909 A | 11/1998 | Cosmescu |
| 5,382,247 A | 1/1995 | Cimino et al. | 5,836,944 A | 11/1998 | Cosmescu |
| 5,385,553 A | 1/1995 | Hart et al. | D402,030 S | 12/1998 | Roberts et al. |
| 5,395,342 A | 3/1995 | Yoon | D402,031 S | 12/1998 | Roberts et al. |
| 5,395,363 A | 3/1995 | Billings et al. | 5,843,109 A | 12/1998 | Mehta et al. |
| 5,399,823 A | 3/1995 | McCusker | 5,846,236 A | 12/1998 | Lindenmeier et al. |
| 5,400,267 A | 3/1995 | Denen et al. | 5,859,527 A | 1/1999 | Cook |
| 5,401,273 A | 3/1995 | Shippert | 5,868,768 A | 2/1999 | Wicherski et al. |
| 5,403,882 A | 4/1995 | Huggins | 5,876,400 A | 3/1999 | Songer |
| 5,406,945 A | 4/1995 | Riazzi et al. | 5,888,200 A | 3/1999 | Walen |
| 5,407,433 A | 4/1995 | Loomas | 5,893,848 A | 4/1999 | Negus et al. |
| 5,409,484 A | 4/1995 | Erlich et al. | 5,893,849 A | 4/1999 | Weaver |
| 5,411,483 A | 5/1995 | Loomas et al. | 5,893,862 A | 4/1999 | Pratt et al. |
| 5,413,575 A | 5/1995 | Haenggi | 5,913,864 A | 6/1999 | Garito et al. |
| 5,421,829 A | 6/1995 | Olichney et al. | 5,919,219 A | 7/1999 | Knowlton |
| 5,423,838 A | 6/1995 | Willard | 5,928,159 A | 7/1999 | Eggers et al. |
| 5,431,645 A | 7/1995 | Smith et al. | 5,938,589 A | 8/1999 | Wako et al. |
| 5,431,650 A | 7/1995 | Cosmescu | 5,941,887 A | 8/1999 | Steen et al. |
| 5,431,667 A | 7/1995 | Thompson et al. | 5,944,737 A | 8/1999 | Tsonton et al. |
| 5,451,222 A | 9/1995 | De Maagd et al. | 5,951,548 A | 9/1999 | DeSisto et al. |
| 5,456,284 A | 10/1995 | Ryan et al. | 5,951,581 A | 9/1999 | Saadat et al. |
| 5,460,602 A | 10/1995 | Shapira | 5,954,686 A | 9/1999 | Garito et al. |

| | | | | | | |
|---|---|---|---|---|---|---|
| 5,972,007 | A | 10/1999 | Sheffield et al. | 6,610,057 B1 | 8/2003 | Ellman et al. |
| 6,004,318 | A | 12/1999 | Garito et al. | 6,616,658 B2 | 9/2003 | Ineson |
| 6,004,333 | A | 12/1999 | Sheffield et al. | 6,618,626 B2 | 9/2003 | West, Jr. et al. |
| 6,004,335 | A | 12/1999 | Vaitekunas et al. | 6,620,161 B2 | 9/2003 | Schulze et al. |
| 6,010,499 | A | 1/2000 | Cobb | 6,622,731 B2 | 9/2003 | Daniel et al. |
| 6,022,347 | A | 2/2000 | Lindenmeier et al. | 6,632,193 B1 | 10/2003 | Davison et al. |
| 6,045,564 | A | 4/2000 | Walen | 6,633,234 B2 | 10/2003 | Wiener et al. |
| 6,063,050 | A | 5/2000 | Manna et al. | 6,652,514 B2 | 11/2003 | Ellman et al. |
| 6,068,603 | A | 5/2000 | Suzuki | 6,662,053 B2 | 12/2003 | Borkan |
| 6,068,627 | A | 5/2000 | Orszulak et al. | 6,669,691 B1 | 12/2003 | Taimisto |
| 6,070,444 | A | 6/2000 | Lontine et al. | 6,676,657 B2 | 1/2004 | Wood |
| 6,071,281 | A | 6/2000 | Burnside et al. | 6,685,701 B2 | 2/2004 | Orszulak et al. |
| 6,074,386 | A | 6/2000 | Goble et al. | 6,685,703 B2 | 2/2004 | Pearson et al. |
| 6,074,387 | A | 6/2000 | Heim et al. | 6,685,704 B2 | 2/2004 | Greep |
| 6,086,544 | A | 7/2000 | Hibner et al. | 6,699,243 B2 | 3/2004 | West et al. |
| 6,090,123 | A | 7/2000 | Culp et al. | 6,702,812 B2 | 3/2004 | Cosmescu |
| 6,099,525 | A | 8/2000 | Cosmescu | 6,710,546 B2 | 3/2004 | Crenshaw |
| 6,117,134 | A | 9/2000 | Cunningham et al. | 6,712,813 B2 | 3/2004 | Ellman et al. |
| 6,139,547 | A | 10/2000 | Lontine et al. | 6,719,746 B2 | 4/2004 | Blanco |
| D433,752 | S | 11/2000 | Saravia | 6,730,079 B2 | 5/2004 | Lovewell |
| 6,142,995 | A | 11/2000 | Cosmescu | 6,740,079 B1 | 5/2004 | Eggers et al. |
| 6,146,353 | A | 11/2000 | Platt, Jr. | 6,747,218 B2 | 6/2004 | Huseman et al. |
| 6,149,648 | A | 11/2000 | Cosmescu | 6,755,825 B2 | 6/2004 | Shoenman et al. |
| 6,156,035 | A | 12/2000 | Songer | D493,530 S | 7/2004 | Reschke |
| 6,197,024 | B1 | 3/2001 | Sullivan | D493,888 S | 8/2004 | Reschke |
| 6,200,311 | B1 | 3/2001 | Danek et al. | D494,270 S | 8/2004 | Reschke |
| D441,077 | S | 4/2001 | Garito et al. | D495,051 S | 8/2004 | Reschke |
| 6,213,999 | B1 | 4/2001 | Platt, Jr. et al. | D495,052 S | 8/2004 | Reschke |
| 6,214,003 | B1 | 4/2001 | Morgan et al. | 6,783,523 B2 | 8/2004 | Qin et al. |
| 6,238,388 | B1 | 5/2001 | Ellman et al. | 6,783,525 B2 | 8/2004 | Greep et al. |
| 6,241,723 | B1 | 6/2001 | Heim et al. | 6,794,929 B2 | 9/2004 | Pelly |
| 6,241,753 | B1 | 6/2001 | Knowlton | 6,827,725 B2 | 12/2004 | Batchelor et al. |
| 6,249,706 | B1 | 6/2001 | Sobota et al. | 6,830,569 B2 | 12/2004 | Thompson et al. |
| 6,251,110 | B1 | 6/2001 | Wampler | 6,832,398 B2 | 12/2004 | Borders et al. |
| 6,257,241 | B1 | 7/2001 | Wampler | 6,840,937 B2 | 1/2005 | Van Wyk |
| 6,258,088 | B1 | 7/2001 | Tzonev et al. | 6,840,948 B2 | 1/2005 | Albrecht et al. |
| 6,270,476 | B1 | 8/2001 | Santoianni et al. | 6,855,140 B2 | 2/2005 | Albrecht et al. |
| 6,273,862 | B1 | 8/2001 | Privitera et al. | 6,855,141 B2 | 2/2005 | Lovewell |
| 6,277,083 | B1 | 8/2001 | Eggers et al. | 6,887,237 B2 | 5/2005 | McGaffigan |
| 6,286,512 | B1 | 9/2001 | Loeb et al. | 6,902,536 B2 | 6/2005 | Manna et al. |
| 6,287,305 | B1 | 9/2001 | Heim et al. | 6,905,496 B1 | 6/2005 | Ellman et al. |
| 6,287,344 | B1 | 9/2001 | Wampler et al. | 6,923,804 B2 | 8/2005 | Eggers et al. |
| 6,312,441 | B1 | 11/2001 | Deng | 6,923,809 B2 | 8/2005 | Eggers et al. |
| 6,325,799 | B1 | 12/2001 | Goble | 6,939,347 B2 | 9/2005 | Thompson |
| D453,222 | S | 1/2002 | Garito et al. | 6,955,674 B2 | 10/2005 | Eick et al. |
| D453,833 | S | 2/2002 | Hess | 6,986,768 B2 | 1/2006 | Allen et al. |
| 6,350,276 | B1 | 2/2002 | Knowlton | D515,412 S | 2/2006 | Waaler et al. |
| 6,352,544 | B1 | 3/2002 | Spitz | 6,994,707 B2 | 2/2006 | Ellman et al. |
| 6,355,034 | B2 | 3/2002 | Cosmescu | 7,004,174 B2 | 2/2006 | Eggers et al. |
| 6,358,281 | B1 | 3/2002 | Berrang et al. | 7,006,874 B2 | 2/2006 | Knowlton et al. |
| 6,361,532 | B1 | 3/2002 | Burek | 7,022,121 B2 | 4/2006 | Stern et al. |
| D457,955 | S | 5/2002 | Bilitz | 7,033,353 B2 | 4/2006 | Stoddard et al. |
| 6,386,032 | B1 | 5/2002 | Lemkin et al. | D521,641 S | 5/2006 | Reschke et al. |
| 6,395,001 | B1 | 5/2002 | Ellman et al. | 7,041,101 B2 | 5/2006 | Eggers |
| 6,402,741 | B1 | 6/2002 | Keppel et al. | 7,044,949 B2 | 5/2006 | Orszulak et al. |
| 6,402,742 | B1 | 6/2002 | Blewett et al. | 7,053,752 B2 | 5/2006 | Wang et al. |
| 6,402,743 | B1 | 6/2002 | Orszulak et al. | 7,060,064 B2 | 6/2006 | Allen et al. |
| 6,402,748 | B1 | 6/2002 | Schoenman et al. | 7,062,317 B2 | 6/2006 | Avrahami et al. |
| 6,409,725 | B1 | 6/2002 | Khandkar et al. | 7,072,703 B2 | 7/2006 | Zhang et al. |
| 6,413,255 | B1 | 7/2002 | Stern | 7,074,218 B2 | 7/2006 | Washington et al. |
| 6,416,491 | B1 | 7/2002 | Edwards et al. | 7,097,640 B2 | 8/2006 | Wang et al. |
| 6,416,509 | B1 | 7/2002 | Goble et al. | 7,112,199 B2 | 9/2006 | Cosmescu |
| 6,425,912 | B1 | 7/2002 | Knowlton | 7,115,121 B2 | 10/2006 | Novak |
| 6,458,122 | B1 | 10/2002 | Pozzato | 7,115,123 B2 | 10/2006 | Knowlton et al. |
| 6,458,125 | B1 | 10/2002 | Cosmescu | 7,125,406 B2 | 10/2006 | Given |
| 6,458,126 | B1 | 10/2002 | Doyle | 7,131,860 B2 | 11/2006 | Sartor et al. |
| 6,461,352 | B2 | 10/2002 | Morgan et al. | 7,141,049 B2 | 11/2006 | Stern et al. |
| 6,464,702 | B2 | 10/2002 | Schulze et al. | D535,396 S | 1/2007 | Reschke et al. |
| 6,471,659 | B2 | 10/2002 | Eggers et al. | 7,156,842 B2 | 1/2007 | Sartor et al. |
| 6,494,882 | B1 | 12/2002 | Lebouitz et al. | 7,156,844 B2 | 1/2007 | Reschke et al. |
| 6,500,169 | B1 | 12/2002 | Deng | 7,166,103 B2 | 1/2007 | Carmel et al. |
| 6,511,479 | B2 | 1/2003 | Gentelia et al. | 7,169,145 B2 | 1/2007 | Isaacson et al. |
| 6,526,320 | B2 | 2/2003 | Mitchell | 7,172,592 B2 | 2/2007 | DeSisto |
| 6,551,313 | B1 | 4/2003 | Levin | 7,189,230 B2 | 3/2007 | Knowlton |
| 6,558,383 | B2 | 5/2003 | Cunningham et al. | 7,204,832 B2 | 4/2007 | Altshuler et al. |
| 6,562,055 | B2 | 5/2003 | Walen | 7,229,436 B2 | 6/2007 | Stern et al. |
| 6,585,664 | B2 | 7/2003 | Burdorff et al. | 7,235,072 B2 | 6/2007 | Sartor et al. |
| 6,589,239 | B2 | 7/2003 | Khandkar et al. | 7,241,294 B2 | 7/2007 | Reschke |
| 6,610,054 | B1 | 8/2003 | Edwards et al. | 7,244,257 B2 | 7/2007 | Podhajsky et al. |

| | | |
|---|---|---|
| 7,267,675 B2 | 9/2007 | Stern et al. |
| 7,267,677 B2 | 9/2007 | Johnson et al. |
| 7,303,556 B2 | 12/2007 | Metzger |
| 7,303,559 B2 | 12/2007 | Peng et al. |
| 7,306,592 B2 | 12/2007 | Morgan et al. |
| 7,311,706 B2 | 12/2007 | Schoenman et al. |
| 7,331,958 B2 | 2/2008 | Falwell et al. |
| 7,367,973 B2 | 5/2008 | Manzo et al. |
| 7,377,919 B2 | 5/2008 | Heim et al. |
| 7,393,354 B2 | 7/2008 | Buchman, II et al. |
| 7,452,358 B2 | 11/2008 | Stern et al. |
| 7,465,309 B2 | 12/2008 | Walen |
| 7,473,251 B2 | 1/2009 | Knowlton et al. |
| 7,500,974 B2 * | 3/2009 | Sartor ............................ 606/45 |
| 7,503,917 B2 | 3/2009 | Sartor et al. |
| 7,563,261 B2 | 7/2009 | Carmel et al. |
| 7,582,244 B2 | 9/2009 | Allen et al. |
| 7,621,909 B2 | 11/2009 | Buchman, II et al. |
| 7,824,408 B2 | 11/2010 | Mirizzi et al. |
| 7,828,794 B2 | 11/2010 | Sartor |
| 7,844,657 B2 | 11/2010 | Novak |
| 7,879,033 B2 | 2/2011 | Sartor et al. |
| 7,955,327 B2 | 6/2011 | Sartor et al. |
| 7,959,633 B2 | 6/2011 | Sartor et al. |
| 8,035,487 B2 | 10/2011 | Malackowski |
| 8,100,902 B2 * | 1/2012 | Sartor ............................ 606/45 |
| 8,128,622 B2 | 3/2012 | Podhajsky et al. |
| 2001/0047183 A1 | 11/2001 | Privitera et al. |
| 2002/0019631 A1 | 2/2002 | Kidder et al. |
| 2002/0026145 A1 | 2/2002 | Bagaoisan et al. |
| 2002/0087079 A1 | 7/2002 | Kaufman et al. |
| 2002/0103485 A1 | 8/2002 | Melnyk et al. |
| 2002/0156471 A1 | 10/2002 | Stern et al. |
| 2003/0109865 A1 | 6/2003 | Greep et al. |
| 2003/0144680 A1 | 7/2003 | Kellogg et al. |
| 2003/0199856 A1 | 10/2003 | Hill et al. |
| 2003/0212393 A1 | 11/2003 | Knowlton et al. |
| 2004/0000316 A1 | 1/2004 | Knowlton et al. |
| 2004/0010246 A1 | 1/2004 | Takahashi |
| 2004/0010248 A1 | 1/2004 | Appling et al. |
| 2004/0015216 A1 | 1/2004 | DeSisto |
| 2004/0030330 A1 | 2/2004 | Brassell et al. |
| 2004/0030367 A1 | 2/2004 | Yamaki et al. |
| 2004/0147909 A1 | 7/2004 | Johnston et al. |
| 2004/0172016 A1 | 9/2004 | Bek et al. |
| 2005/0059858 A1 | 3/2005 | Frith et al. |
| 2005/0059967 A1 | 3/2005 | Breazeale, Jr. et al. |
| 2005/0085804 A1 | 4/2005 | McGaffigan |
| 2005/0096645 A1 | 5/2005 | Wellman et al. |
| 2005/0096646 A1 | 5/2005 | Wellman et al. |
| 2005/0096681 A1 | 5/2005 | Desinger et al. |
| 2005/0113824 A1 | 5/2005 | Sartor et al. |
| 2005/0149001 A1 | 7/2005 | Uchikubo et al. |
| 2006/0241577 A1 | 10/2006 | Balbierz et al. |
| 2007/0049914 A1 | 3/2007 | Eggleston |
| 2007/0260240 A1 | 11/2007 | Rusin |
| 2009/0143778 A1 | 6/2009 | Sartor et al. |
| 2009/0149851 A1 | 6/2009 | Craig |
| 2009/0248008 A1 | 10/2009 | Kerr |
| 2009/0248010 A1 | 10/2009 | Fry et al. |
| 2009/0248015 A1 | 10/2009 | Heard et al. |
| 2009/0248016 A1 | 10/2009 | Heard |
| 2009/0248017 A1 | 10/2009 | Heard |
| 2009/0248018 A1 | 10/2009 | Kerr |
| 2009/0322034 A1 | 12/2009 | Cunningham et al. |
| 2010/0114087 A1 | 5/2010 | Edwards et al. |
| 2010/0204696 A1 | 8/2010 | Mathonnet |

| | | |
|---|---|---|
| 2011/0034921 A1 | 2/2011 | Sartor |
| 2011/0054461 A1 | 3/2011 | Dickhans |
| 2011/0092971 A1 | 4/2011 | Sartor et al. |

FOREIGN PATENT DOCUMENTS

| | | |
|---|---|---|
| DE | 30 45 996 | 7/1982 |
| EP | 0186369 A | 7/1986 |
| EP | 1050277 | 11/2000 |
| EP | 1050279 | 11/2000 |
| EP | 1082945 | 3/2001 |
| EP | 1293171 | 3/2003 |
| EP | 1645233 | 4/2006 |
| EP | 1645234 | 4/2006 |
| EP | 1656900 | 5/2006 |
| EP | 1852078 | 11/2007 |
| FR | 2235669 | 1/1975 |
| FR | 2798579 | 3/2001 |
| JP | 55000243 | 1/1980 |
| JP | 63082710 | 4/1988 |
| WO | WO 93/04717 | 3/1993 |
| WO | WO 94/20032 | 9/1994 |
| WO | WO 95/13023 | 5/1995 |
| WO | WO 96/04936 | 2/1996 |
| WO | WO 96/39086 | 12/1996 |
| WO | WO 97/04761 | 2/1997 |
| WO | WO 97/47249 | 12/1997 |
| WO | WO 98/43264 | 10/1998 |
| WO | WO 98/53865 | 12/1998 |
| WO | WO 01/64122 | 9/2001 |
| WO | WO 02/47568 | 6/2002 |
| WO | WO 2004/010883 | 2/2004 |
| WO | WO 2004/045436 | 6/2004 |
| WO | WO 2004/073753 A2 | 9/2004 |
| WO | WO 2005/060849 | 7/2005 |
| WO | WO 2009/124063 | 10/2009 |

OTHER PUBLICATIONS

International Search Report EP 05019882.9 dated Feb. 16, 2006.
International Search Report EP 05021777.7 dated Feb. 23, 2006.
International Search Report EP 06005540 dated Sep. 24, 2007.
International Search Report EP 06006908 dated Feb. 25, 2009.
International Search Report EP 06014461.5 dated Oct. 31, 2006.
International Search Report EP 07009028 dated Jul. 16, 2007.
International Search Report EP 08002357 dated Jun. 30, 2008.
International Search Report EP 08021070 dated Apr. 1, 2009.
International Search Report EP 10153021 dated Apr. 14, 2010.
International Search Report EP 10153021-extended dated Nov. 12, 2010.
International Search Report EP 10175050.3 dated Dec. 20, 2010.
International Search Report PCT-US03/22900 dated Nov. 20, 2003.
International Search Report PCT-US03/37111 dated Jul. 21, 2004.
International Search Report PCT-US04/04685 dated Aug. 6, 2004.
Li et al., "Interactive Catheter Shape Modeling in Interventional Radiology Simulation" 2001, Springer, Berlin/Heidelberg vol. 2208, pp. 457-464.
Zucker, Karl, "Surgical Laparoscopy", Lippincott Williams & Wilkins, Ed. 2, 2001 (2 pages).
International Search Report corresponding to European Application No. EP 10180957.2, dated May 31, 2012.
International Search Report corresponding to European Application No. EP 06013242.0, dated Oct. 17, 2006.
Official Action issued by the EP Patent Office in co-pending European Application No. 06013242.0, dated Feb. 12, 2010.

* cited by examiner

ELECTRODE WITH ROTATABLY DEPLOYABLE SHEATH

CROSS-REFERENCE TO RELATED APPLICATION

The present application is a Continuation Application claiming the benefit of and priority to U.S. application Ser. No. 12/363,322, now U.S. Pat. No. 8,100,902, filed on Jan. 30, 2009, which is a Continuation Application claiming the benefit of and priority to U.S. application Ser. No. 11/168,901, now U.S. Pat. No. 7,500,974, filed on Jun. 28, 2005, the entire content of which is incorporated herein by reference.

BACKGROUND

1. Technical Field

The present disclosure relates generally to electrosurgical instruments and, more particularly, to an electrode including a selectively deployable protective sheath.

2. Background of Related Art

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, which transfer radio-frequency (RF) electrical or electrosurgical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical cutting and fulguration.

In particular, electrosurgical fulguration includes the application of electric spark to biological tissue, for example, human flesh or the tissue of internal organs, without significant cutting. The spark is produced by bursts of radio-frequency electrical or electrosurgical energy generated from an appropriate electrosurgical generator. Coagulation is defined as a process of desiccating tissue wherein the tissue cells are ruptured and dehydrated/dried. Electrosurgical cutting/dissecting, on the other hand, includes applying an electrical spark to tissue in order to produce a cutting, dissecting and/or dividing effect. Blending includes the function of cutting/dissecting combined with the production of a hemostasis effect. Meanwhile, sealing/hemostasis is defined as the process of liquefying the collagen in the tissue so that it forms into a fused mass.

As used herein the term "electrosurgical pencil" is intended to include instruments which have a handpiece which is attached to an active electrode and which is used to cauterize, coagulate and/or cut tissue. Typically, the electrosurgical pencil may be operated by a handswitch or a foot switch. The active electrode is an electrically conducting element which is usually elongated and may be in the form of a thin flat blade with a pointed or rounded distal end. Alternatively, the active electrode may include an elongated narrow cylindrical needle which is solid or hollow with a flat, rounded, pointed or slanted distal end. Typically electrodes of this sort are known in the art as "blade", "loop" or "snare", "needle" or "ball" electrodes.

As mentioned above, the handpiece of the electrosurgical pencil is connected to a suitable electrosurgical energy source (i.e., generator) which produces the radio-frequency electrical energy necessary for the operation of the electrosurgical pencil. In general, when an operation is performed on a patient with an electrosurgical pencil, electrical energy from the electrosurgical generator is conducted through the active electrode to the tissue at the site of the operation and then through the patient to a return electrode. The return electrode is typically placed at a convenient place on the patient's body and is attached to the generator by a conductive material. Typically, the surgeon activates the controls on the electrosurgical pencil to select the modes/waveforms to achieve a desired surgical effect. Typically, the "modes" relate to the various electrical waveforms, e.g., a cutting waveform has a tendency to cut tissue, a coagulating wave form has a tendency to coagulate tissue, and a blend wave form tends to be somewhere between a cut and coagulate wave from. The power or energy parameters are typically controlled from outside the sterile field which requires an intermediary like a circulating nurse to make such adjustment.

A typical electrosurgical generator has numerous controls for selecting an electrosurgical output. For example, the surgeon can select various surgical "modes" to treat tissue: cut, blend (blend levels 1-3), low cut, desiccate, fulgurate, spray, etc. The surgeon also has the option of selecting a range of power settings typically ranging from 1-300 W. As can be appreciated, this gives the surgeon a great deal of variety when treating tissue.

In particular with the use of active electrodes having a sharpened or pointed tip, a need exists for electrosurgical instruments (i.e., electrosurgical pencils) including incorporated safety features, elements and/or systems to protect the user from inadvertent or accidental pricking and/or stabbing by the active electrode.

SUMMARY

According to an aspect of the present disclosure, a sheath system for selectively covering a distal end of an electrocautery blade is provided. The sheath system includes a hub having a body portion defining a lumen therethrough; and a sheath having a body portion defining a lumen therethrough. The lumen of the sheath is configured and dimensioned to operatively receive an electrocautery blade therein. The sheath is translatably associated with the hub such that rotation of the hub in a first direction results in axial movement of the sheath in a first direction to expose a distal end of the electrocautery blade and rotation of the hub in a second direction, opposite to the first direction, results in axial movement of the sheath in a second direction to cover the distal end of the electrocautery blade. It is envisioned that the hub and the sheath are concentric with one another.

The body portion of the hub may include at least one helical groove formed in an inner surface thereof. Meanwhile, the body portion of the sheath includes at least one nub extending from an outer surface thereof. The nub may be configured and dimensioned to slidably engage the groove of the hub. Accordingly, as the hub is rotated, the nub of the sheath rides along the helical groove of the hub to translate the sheath in one of a distal and proximal direction.

The sheath system further includes a collar configured and dimensioned to support the electrocautery blade. Each of a distal end and a proximal end of the electrocautery blade extends from a respective distal and proximal end of the collar. At least a portion of the collar is rotatably supported in the body portion of the hub and a portion of the collar is disposed in the lumen of the sheath. The collar may include an annular flange extending from an outer surface thereof, and the hub may include an annular groove formed in an inner surface of the body portion. As such, the annular groove of the hub is configured and dimensioned to slidably receive the annular flange of the collar.

It is envisioned that the body portion of the sheath may include an elongated slot formed therein and the collar may include a stub extending from the outer surface thereof. In an embodiment, the stub of the collar is configured and dimensioned to slidably engage the elongated slot formed in the body portion of the sheath. Accordingly, the inter-engagement of the stub of the collar in the elongate slot of the sheath prevents rotation of the sheath as the hub is rotated.

It is contemplated that at least a portion of each of the hub, the sheath and the connector is fabricated from non-conductive materials. It is further contemplated that the body portion of the hub includes finger grips.

According to another aspect of the present disclosure, a sheath system for selectively covering a distal end of an electrocautery blade is provided. The sheath system includes a hub having a body portion defining a lumen therethrough. The body portion of the hub includes a helical groove and an annular groove formed therein. The annular groove is formed at a location proximal of the helical groove.

The sheath system further includes a sheath having a body portion defining a lumen therethrough. The body portion of the sheath includes a nub extending from an outer surface thereof, wherein the nub is configured and dimensioned to slidably engage the helical groove formed in the hub; and an elongated slot formed therein. The sheath is translatably associated with the hub such that rotation of the hub in a first direction results in axial movement of the sheath in a first direction to expose a distal end of the electrocautery blade and rotation of the hub in a second direction, opposite to the first direction, results in axial movement of the sheath in a second direction to cover the distal end of the electrocautery blade.

The sheath system further includes a collar configured and dimensioned for support on the electrocautery blade. A distal end and a proximal end of the electrocautery blade each extend from a respective distal end and proximal end of the collar. It is envisioned that at least a portion of the collar is rotatably supported in the body portion of the hub and a portion of the collar is disposed in the lumen of the sheath. The collar desirably includes an annular flange extending from an outer surface thereof for slidable engagement in the annular groove formed in the hub; and a stub extending from the outer surface of thereof at a location distal of the annular flange for slidable engagement in the elongate slot of the sheath. Accordingly, rotation of the hub a first direction results in axial movement of the sheath in a first direction to expose a distal end of the electrocautery blade and rotation of the hub in a second direction, opposite to the first direction, results in axial movement of the sheath in a second direction to cover the distal end of the electrocautery blade.

It is envisioned that the hub, the sheath, and the collar are concentric with one another. It is contemplated that at least a portion of each of the hub, the sheath and the connector is fabricated from non-conductive materials. Desirably, the body portion of the hub includes finger grips.

In operation, as the hub is rotated, the nub of the sheath rides along the helical groove of the hub to translate the sheath in one of a distal and proximal direction. Additionally, the inter-engagement of the stub of the collar in the elongated slot of the sheath prevents the rotation of the sheath as the hub is rotated.

According to yet another aspect of the present disclosure, an electrosurgical pencil for electrical connection to an electrosurgical generator is provided. The electrosurgical pencil includes an elongate housing; an electrocautery blade including a proximal end supported in the housing, and a distal end extending distally from the housing, the electrocautery blade being electrically connectable with the electrosurgical generator; at least one activation switch supported on the housing, each activation switch being configured and adapted to selectively activate the electrosurgical pencil; and a sheath system for selectively covering and exposing the distal end of the electrocautery blade.

The sheath system includes a hub having a body portion defining a lumen therethrough; and a sheath including a body portion defining a lumen therethrough. The lumen of the sheath is configured and dimensioned to operatively receive the electrocautery blade therein. The sheath is translatably associated with the hub such that rotation of the hub in a first direction results in axial movement of the sheath in a first direction to expose the distal end of the electrocautery blade and rotation of the hub in a second direction, opposite to the first direction, results in axial movement of the sheath in a second direction to cover the distal end of the electrocautery blade.

In this embodiment, it is envisioned that the hub and the sheath are concentric with one another.

The body portion of the hub may include at least one helical groove formed in an inner surface thereof; and the body portion of the sheath desirably includes at least one nub extending from an outer surface thereof. It is envisioned that the nub is configured and dimensioned to slidably engage the groove of the hub. Accordingly, as the hub is rotated, the nub of the sheath rides along the helical groove of the hub to translate the sheath in one of a distal and proximal direction.

The sheath system further includes a collar configured and dimensioned for support on the electrocautery blade, wherein each of the distal end and the proximal end of the electrocautery blade extends from a respective distal and proximal end of the collar. At least a portion of the collar is rotatably supported in the body portion of the hub and at least a portion of the collar is disposed in the lumen of the sheath.

Desirably, the collar includes an annular flange extending from an outer surface thereof, and the hub desirably includes an annular groove formed in an inner surface of the body portion. It is envisioned that the annular groove of the hub is configured and dimensioned to slidably receive the annular flange of the collar.

Desirably, the body portion of the sheath includes an elongate slot formed therein, and the collar includes a stub extending from the outer surface thereof. It is envisioned that the stub of the collar is configured and dimensioned to slidably engage the elongate slot formed in the body portion of the sheath. In use, the inter-engagement of the stub of the collar in the elongate slot of the sheath prevents the rotation of the sheath as the hub is rotated.

According to still another aspect of the present disclosure, a sheath system for selectively covering a distal end of an electrocautery blade is provided. It is envisioned that the electrocautery blade may be electrically connectable to an electrosurgical device and may be capable of transmitting electrosurgical energy. The sheath system includes an electrocautery blade having a distal end and a proximal end; a collar configured and dimensioned for support on the electrocautery blade; a sheath operatively supported on a distal end of the collar; and a hub operatively supported on the sheath and on a proximal end of the collar.

Desirably, the distal end and the proximal end of the electrocautery blade each extend from a respective distal and proximal end of the collar. The collar includes an annular flange extending from an outer surface thereof; and a stub extending from the outer surface thereof at a location distal of the annular flange.

Desirably, the sheath includes a body portion defining a lumen therethrough; a nub extending from an outer surface of the body portion of the sheath; and an elongated slot formed in the body portion of the sheath for slidably receiving the stub of the collar therein.

Desirably, the hub includes a body portion defining a lumen therethrough. The body portion of the hub includes a helical groove formed therein for slidably engaging the nub of the collar and an annular groove formed therein for rotatably receiving the annular flange of the collar. The annular groove is formed at a location proximal of the helical groove.

Desirably, the sheath is translatably associated with the hub such that rotation of the hub in a first direction results in axial movement of the sheath in a first direction to expose a distal end of the electrocautery blade, and rotation of the hub in a second direction, opposite to the first direction, results in axial movement of the sheath in a second direction to cover the distal end of the electrocautery blade.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

DETAILED DESCRIPTION

Figure 1:
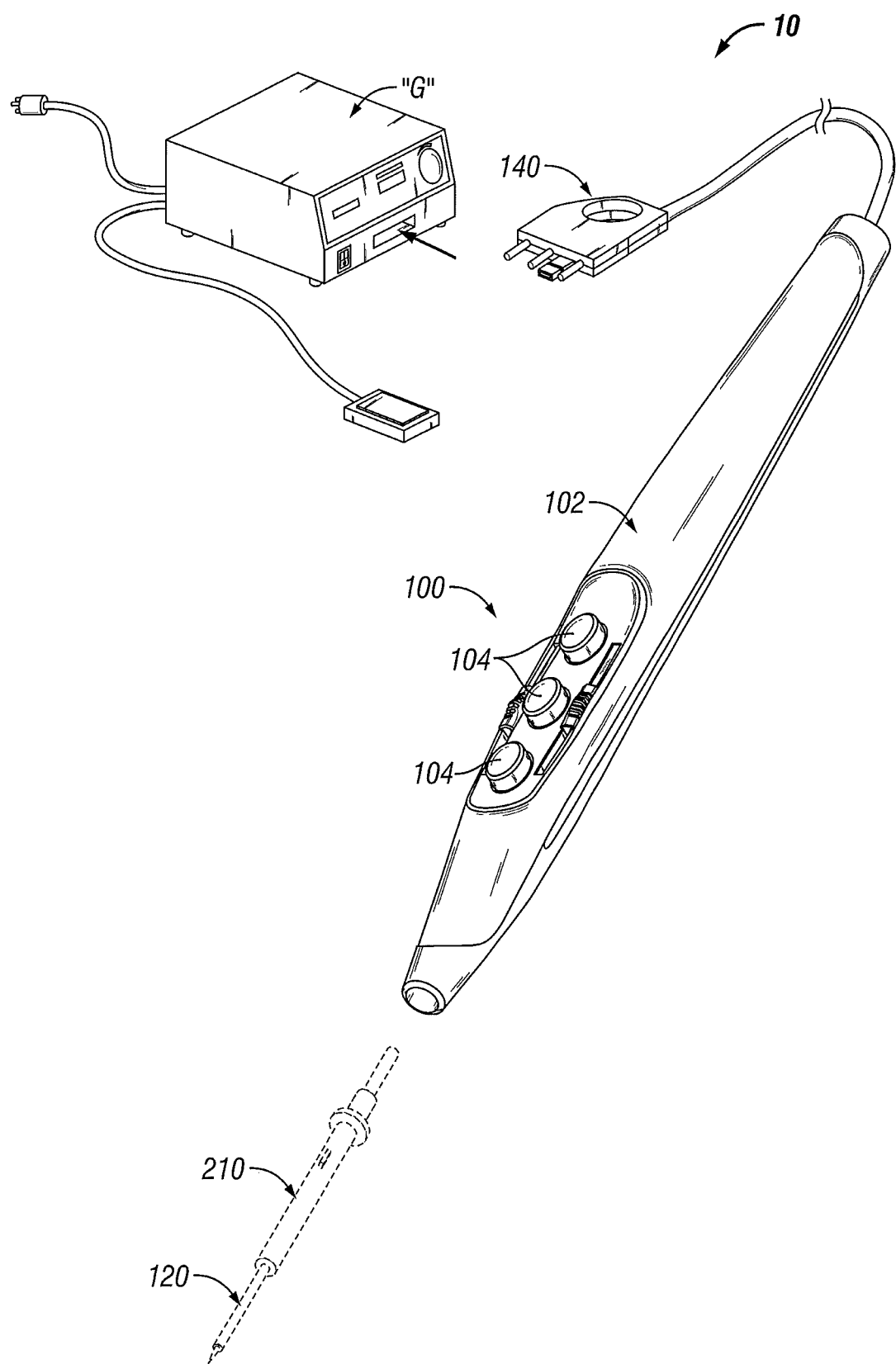
FIG. 1 is a perspective view of a typical electrosurgical system.

Particular embodiments of the presently disclosed electrosurgical pencil and sheath system will now be described in detail with reference to the drawing figures wherein like reference numerals identify similar or identical elements. As used herein, the term "distal" refers to that portion which is further from the user while the term "proximal" refers to that portion which is closer to the user or surgeon.

Referring initially to FIG. 1, there is seen a perspective view of an electrosurgical instrument system in accordance with an embodiment of the present disclosure, generally indicated as reference numeral 10. Electrosurgical instrument system 10 includes an electrosurgical instrument 100 constructed in accordance with an embodiment of the present disclosure. While the following description will be directed towards electrosurgical pencils including sharpened or pointed electrocautery blades and the like, it is envisioned that the features and concepts (or portions thereof) of the present disclosure can be applied to electrosurgical pencils including any type of electrocautery blade.

Electrosurgical pencil 100 includes a housing 102 configured and adapted to support a sheath system 200 (FIGS. 2-8) at a distal end thereof which, in turn, receives a replaceable electrode or electrocautery blade 120 therein. Electrosurgical pencil 100 further includes at least one activation button 104 supported on an outer surface of housing 102. Activation button(s) 104 are operable to control the supply of RF electrical energy to blade 120 from an electrosurgical generator "G". Electrosurgical pencil 100 may be coupled to electrosurgical generator "G" via a plug assembly 140.

Other electrosurgical pencils which may incorporate and/or include the sheath system disclosed herein are identified in U.S. patent application Ser. No. 10/959,824, filed on Oct. 6, 2004, entitled "Electrosurgical Pencil with Improved Controls"; and International Application No. PCT/US03/37111, filed on Nov. 20, 2003, also entitled "Electrosurgical Pencil with Improved Controls", the entire contents of each of which being incorporated by reference herein.

By way of example only, electrosurgical generator "G" may be any one of the following, or equivalents thereof: the "FORCE FX", "FORCE 2" or "FORCE 4" generators manufactured by Valleylab, Inc. of Boulder, Colo., a Division of Tyco Healthcare LP. It is contemplated that electrosurgical generator "G" can be preset to selectively provide an appropriate first predetermined RF signal (e.g., about 1 to 300 watts) for tissue cutting and an appropriate second predetermined RF signal (e.g., about 1 to 120 watts) for tissue coagulation. However, electrosurgical generator "G" may be adapted to automatically configure itself to transmit particular RF signals depending on the particular electrosurgical instrument connected thereto.

Figure 2:
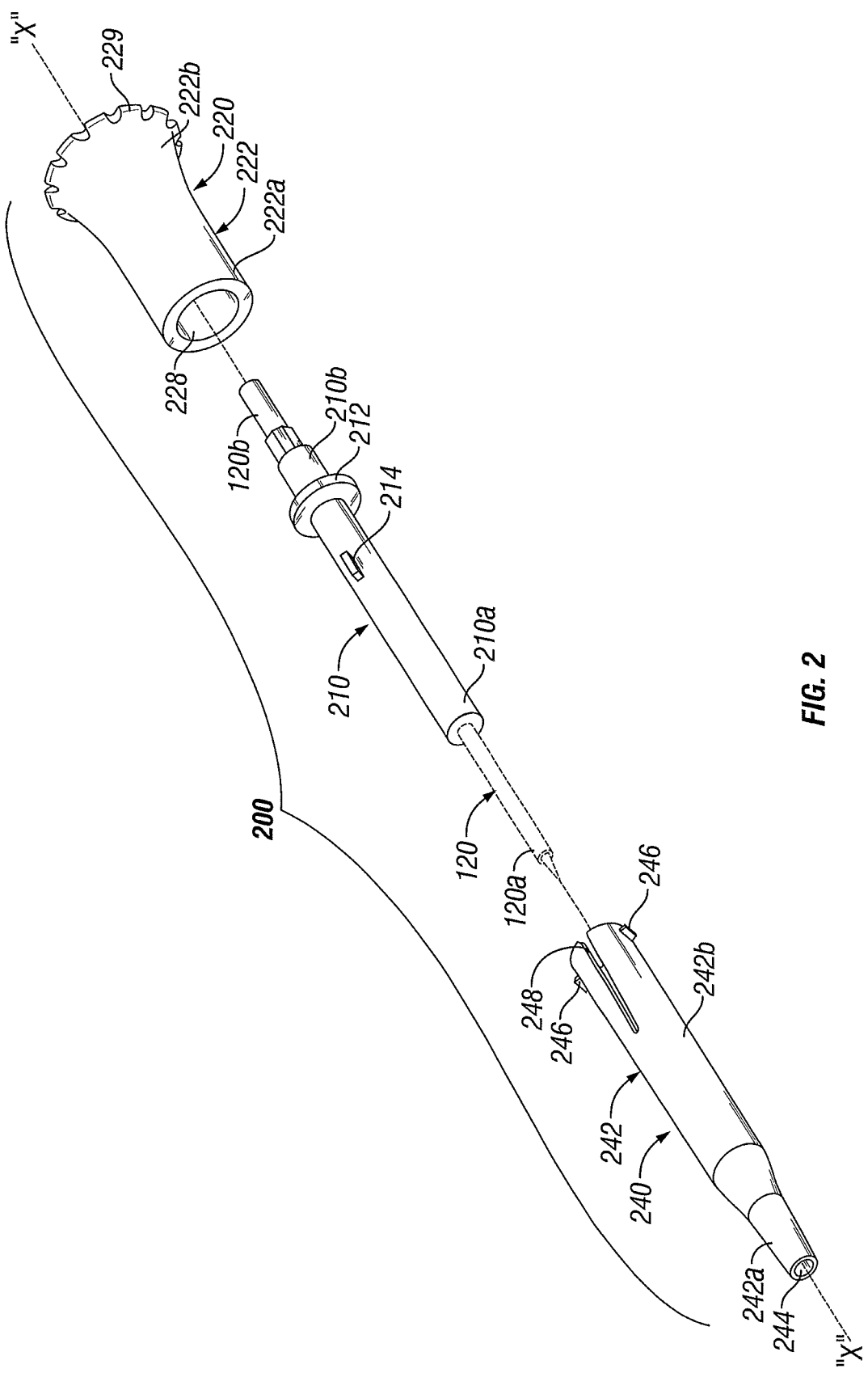
FIG. 2 is a perspective view, with parts separated, of the sheath system of FIG. 1.
Figure 3:
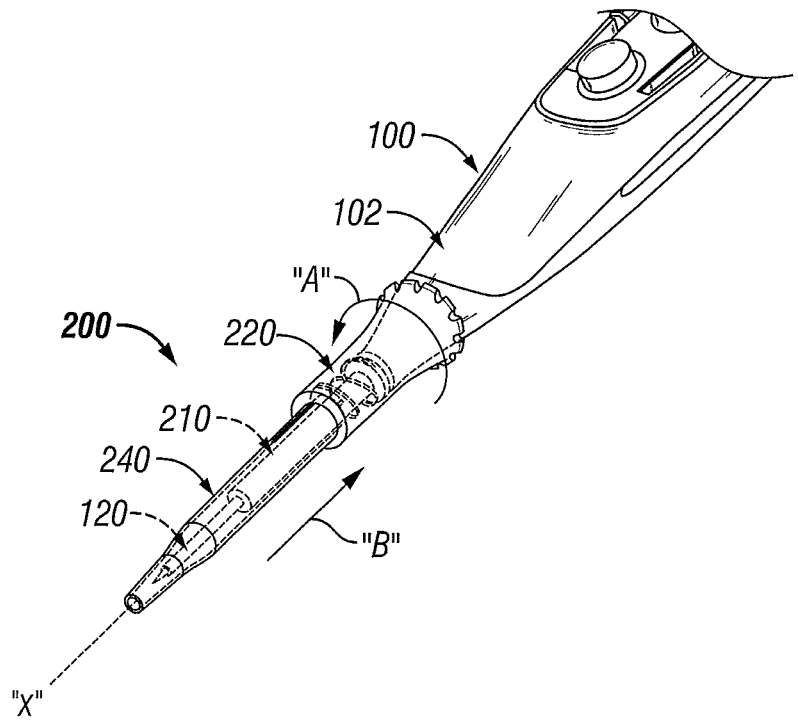
FIG. 3 is a perspective view of a distal end of an electrosurgical pencil of FIG. 1 illustrating the sheath system in a deployed or covering position.
Figure 4:
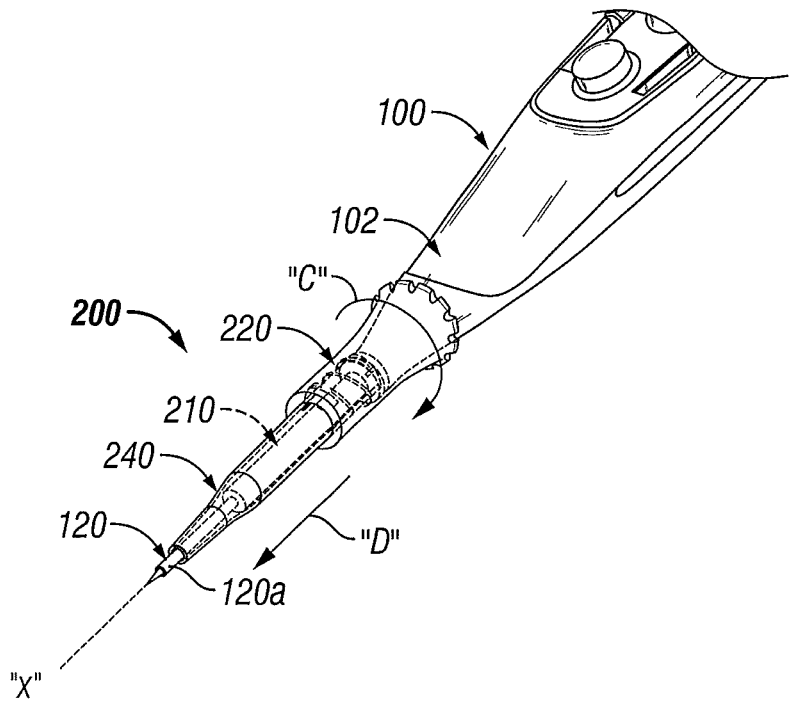
FIG. 4 is a perspective view of the distal end of the electrosurgical pencil of FIG. 1 illustrating the sheath system in a retracted or exposing condition.
Figure 5:
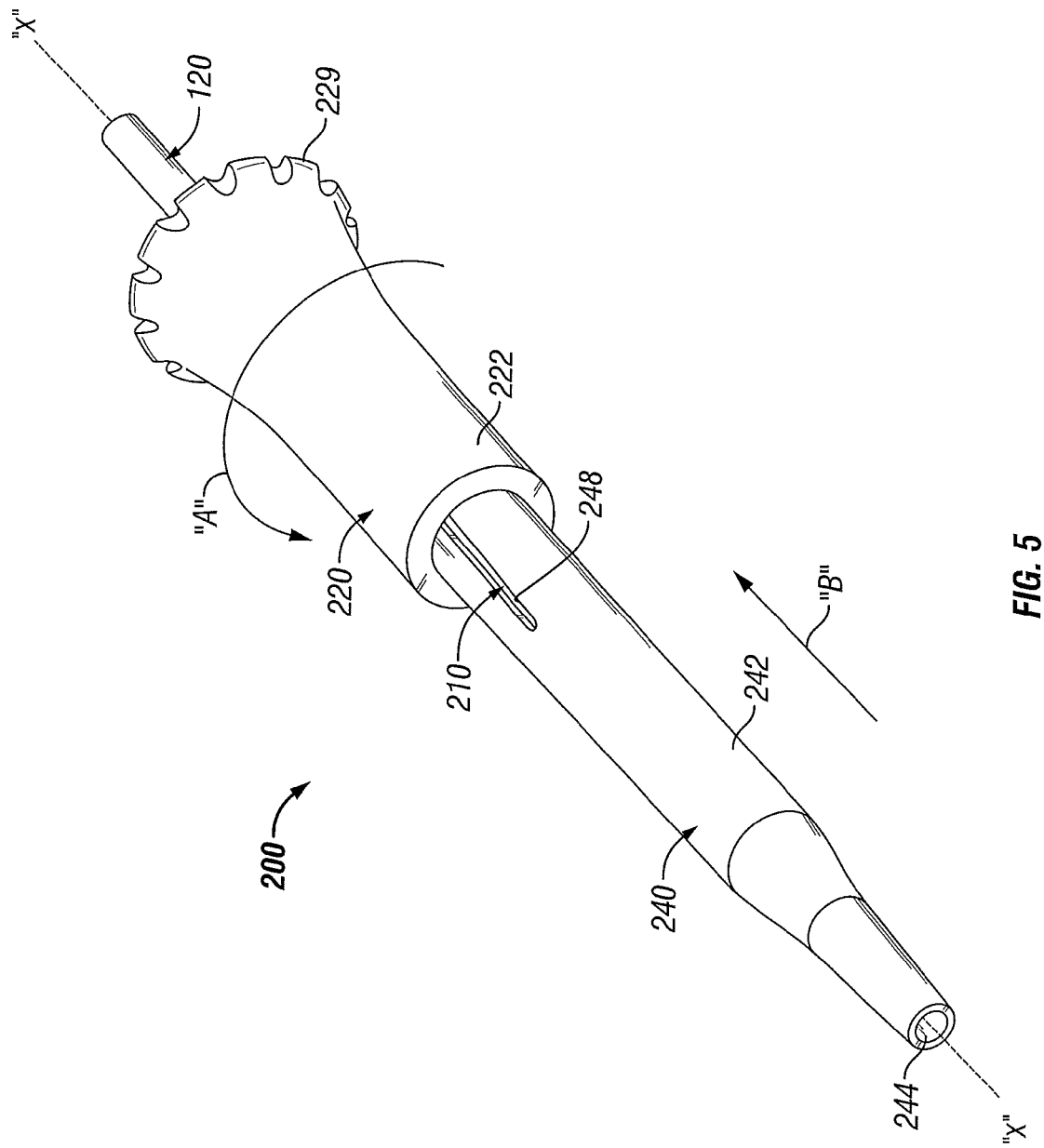
FIG. 5 is an enlarged perspective view of the sheath system of FIGS. 2-4, shown in the deployed or covering position.
Figure 6:
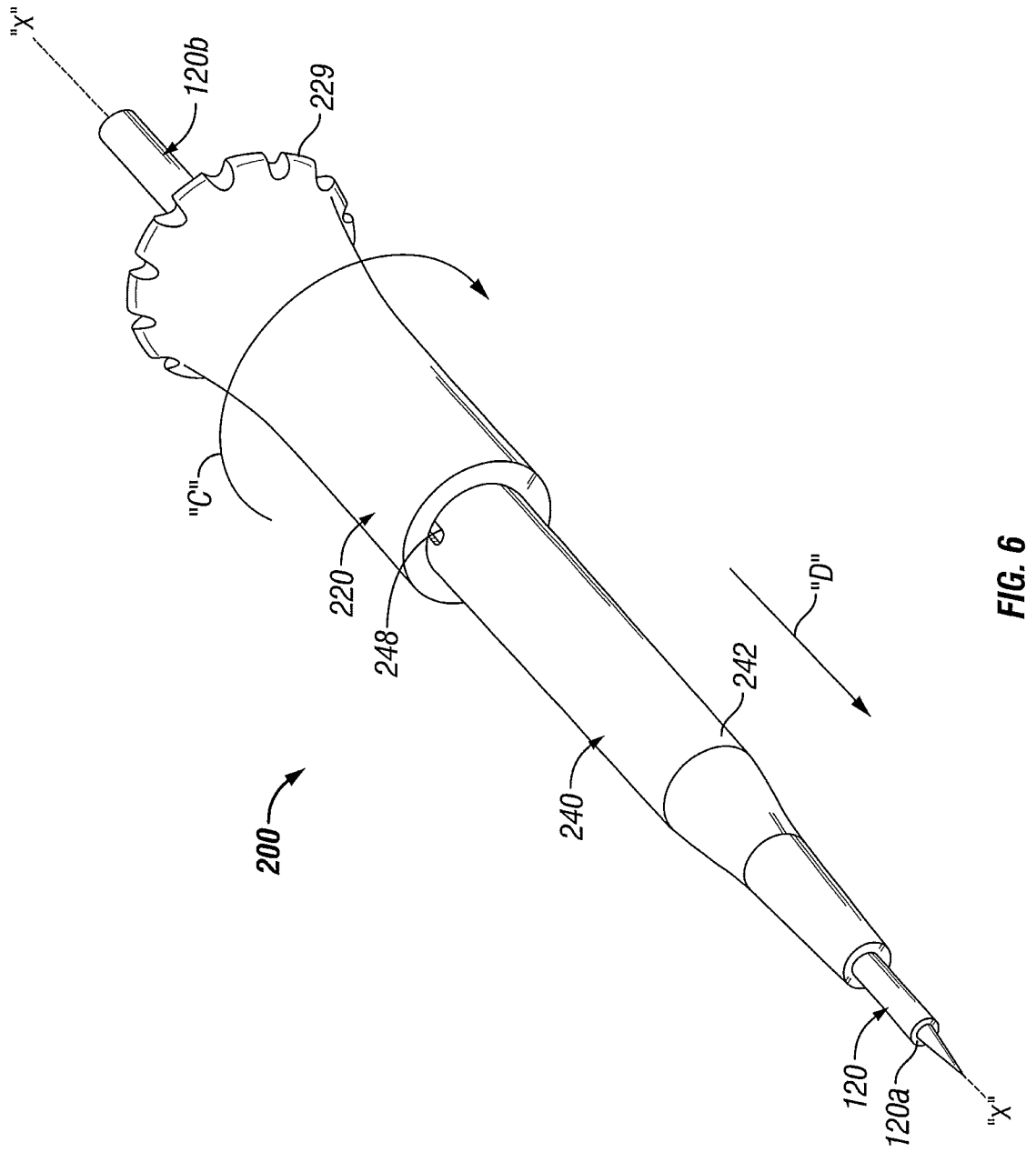
FIG. 6 is an enlarged perspective view of the sheath system of FIGS. 2-5, shown in the retracted or exposing condition.

Turning now to FIGS. 2-8, a sheath system for electrosurgical pencil 100, in accordance with an embodiment of the present disclosure, is generally designated as 200. Sheath system 200 is operatively supportable on a distal end of housing 102 of electrosurgical pencil 100. Sheath system 200 includes at least a first position in which sheath system 200 is deployed to completely cover electrocautery blade 120, as seen in FIGS. 3 and 5, and a second position in which sheath system 200 is retracted to expose electrocautery blade 120, as seen in FIGS. 4 and 6.

Figure 7:
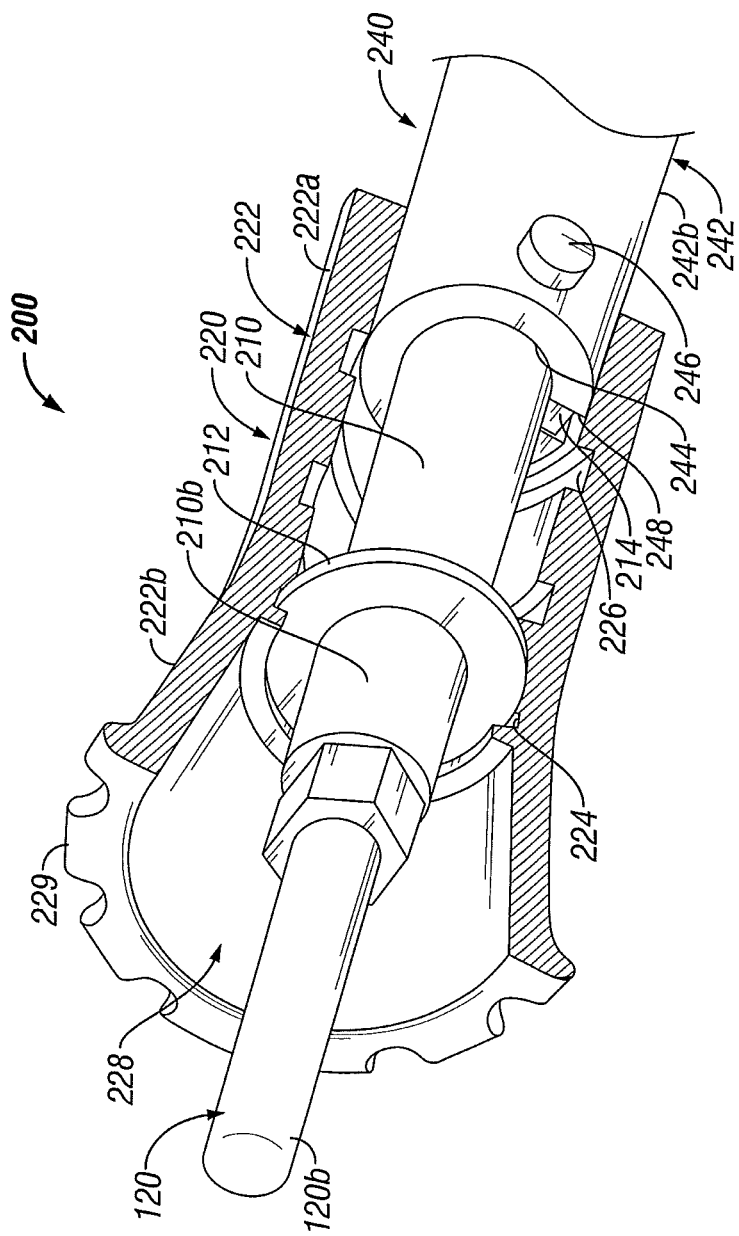
FIG. 7 is a rear, perspective, partial cross-sectional view of the sheath system of FIGS. 2-6.
Figure 8:
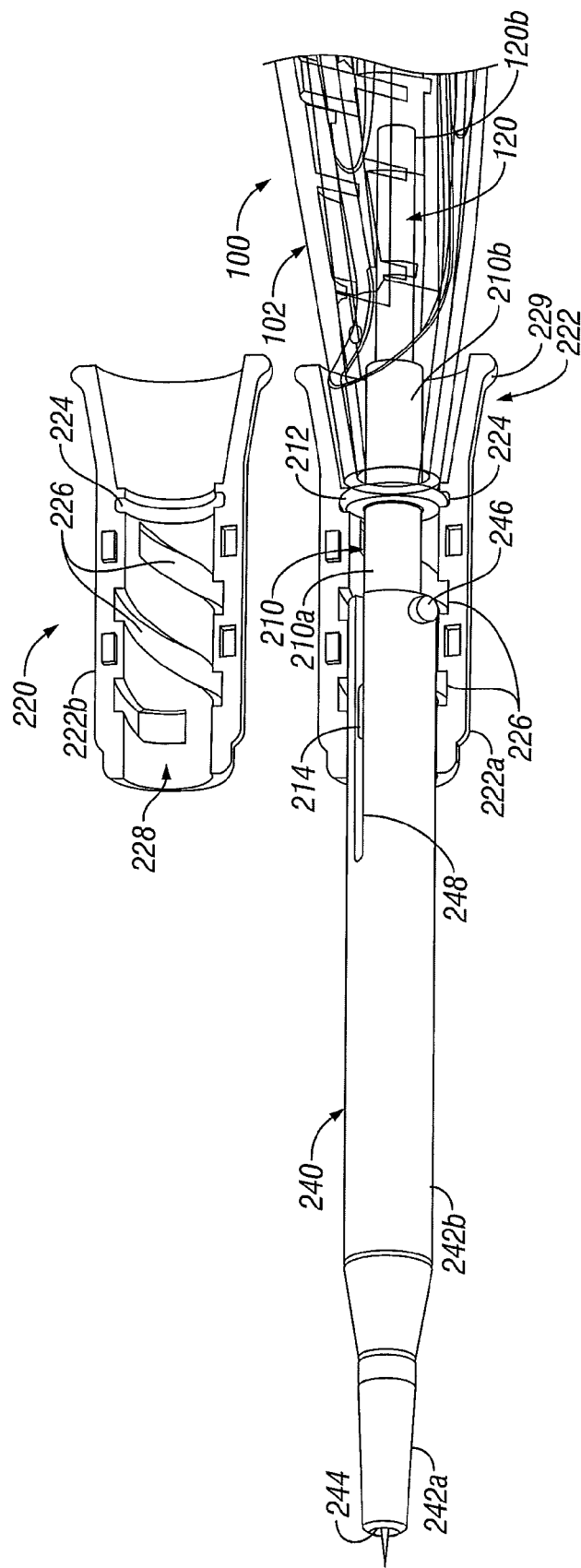
FIG. 8 is a perspective view of a distal end of an electrosurgical pencil of FIG. 1 illustrating the hub of the sheath system in a separated condition.

As seen in FIGS. 2, 7 and 8, sheath system 200 includes an elongate collar 210 configured and dimensioned to receive and support electrocautery blade 120. Desirably, collar 210 is dimensioned such that a distal end 120a of electrocautery blade 120 extends from a distal end 210a thereof, and a proximal end 120b of electrocautery blade 120 extends from a proximal end 210b thereof. Collar 210 includes an annular flange 212 extending therearound.

As seen in FIGS. 2-8, sheath system 200 further includes a hub 220 rotatably supportable at the distal end of housing 102; and a protective sheath 240 operatively connected to hub 220 in such a manner that as hub 220 is rotated, sheath 240 is displaced axially (i.e., either proximally or distally). As seen in FIG. 7, hub 220 includes an internal annular groove 224 formed in a body portion 222 thereof for rotatably receiving and supporting annular flange 212 of collar 210.

Body portion 222 of hub 220 includes a substantially cylindrical distal portion 222a and a flared or substantially frustoconical proximal portion 222b. Flared proximal portion 222b is configured and dimensioned to approximate the taper and/or outer profile of the distal end of housing 102 of electrosurgical pencil 100. As mentioned above, collar 210 and, in turn, electrocautery blade 120, is rotatably supported in a lumen 228 defined by body portion 222 of hub 220.

As seen in FIGS. 7 and 8, hub 220 includes a helical groove 226 formed along an inner periphery thereof. Helical groove 226 is formed in an inner surface of distal portion 222*a* at a location distal to annular groove 224.

With continued reference to FIGS. 2-8, sheath 240 includes a body portion 242 defining a lumen 244 therethrough. Body portion 242 of sheath 240 desirably includes a tapered distal portion 242*a*, and a substantially cylindrical proximal portion 242*b*. Lumen 244 of sheath 240 is configured and dimensioned to operatively receive distal end 120*a* of electrocautery blade 120 and distal end 210*a* of collar 210 therein.

As seen in FIGS. 2, 7 and 8, sheath 240 includes at least one nub 246 projecting from an outer surface of body portion 242. A pair of diametrically opposed nubs 246 project from proximal portion 242*b* of body portion 242. Each nub 246 is configured and dimensioned to slidably seat within helical groove 226 formed in the inner surface of body portion 222 of hub 220. As will be described in greater detail below, nubs 246 cause sheath 240 to move distally and proximally as hub 220 is rotated in a clockwise or counter-clockwise direction.

Sheath 240 includes a longitudinally oriented elongate slot 248 formed in at least the proximal portion 242*b* of body portion 242. Elongate slot 248 is configured and dimensioned to slidably receive a stub 214 projecting from an outer surface of collar 210. As will be described in greater detail below, stub 214 of collar 210 prevents sheath 240 from rotating about a longitudinal axis as hub 220 is rotated.

Sheath 240 includes at least a first position in which sheath 240 is deployed to completely cover electrocautery blade 120, as seen in FIGS. 3 and 5, and at least a second position in which sheath 240 is retracted to expose at least the distal end 120*a* of electrocautery blade 120, as seen in FIGS. 4 and 6.

Each of collar 210, hub 220 and sheath 240 are fabricated from electrically non-conductive and/or insulative materials. In this manner, sheath system 200 does not electrically short electrocautery blade 120.

It is further desired for hub 220 to be provided with finger tabs or grips 229 formed around and along at least a portion of, preferably around and along substantially the entire length, a proximal edge of body portion 222. Grips 229 increase the users ability to rotate hub 220 about a longitudinal axis relative to housing 102 of electrosurgical pencil 100.

As seen in FIG. 2, collar 210, hub 220 and sheath 240 share a common longitudinal "X" axis. A central axis of electrocautery blade 120 is axially aligned with the longitudinal "X" axis. Additionally, a central axis of collar 210, a central axis of lumen 228 of hub 220, and a central axis of lumen 244 of sheath 240 are axially aligned with the longitudinal "X" axis. As will be described in greater detail below, hub 220 is rotatable about the longitudinal "X" axis and sheath 240 is translatable along the longitudinal "X" axis. In an embodiment, sheath 240 is concentrically aligned with hub 220.

When sheath system 200 is in the first or deployed condition, nubs 246 of sheath 240 at located at or near a distal end of helical groove 226 formed in hub 220. Additionally, stub 214 of collar 210 is located at or near a distal end of elongate slot 248 formed in proximal portion 242*b* of body portion 242. When sheath system 200 is in the second or retracted condition, nubs 246 of sheath 240 are located at or near a proximal of helical groove 226 formed in hub 220. Additionally, stub 214 of collar 210 is located at or near a proximal end of elongate slot 248 formed in proximal portion 242*b* of body portion 242.

Sheath system 200 is operatively connected to electrocautery blade 120 in such a manner that proximal end 120*b* of electrocautery blade 120 extends from hub 220. When electrocautery blade 120 is connected to electrosurgical pencil 100, sheath system 200 is necessarily operatively associated with electrosurgical pencil 100. In particular, when electrocautery blade 120 is operatively connected to electrosurgical pencil 100, proximal end 120*b* of electrocautery blade 120 enters an open distal end of housing 102 of electrosurgical pencil 100 and electrically engages and/or is connected to a blade receptacle (not shown) provided in electrosurgical pencil 100. A shaped portion 211*b*, preferably hex-shaped, of a proximal end 210*b* of collar 210 engages a complementary shaped recess (not shown) formed in housing 102 of electrosurgical pencil 100 to prevent rotation of blade 120 when properly coupled thereto. Additionally, a distal end of housing 102 of electrosurgical pencil 100 is positioned in lumen 228 of flared proximal portion 222*b* of body portion 222 of hub 220.

With continued reference to FIGS. 2-8, a method of operating sheath system 200 to expose and cover distal end 120*a* of electrocautery blade 120 is shown and described. Electrocautery blade 120 may be connected or coupled to and disconnected from electrosurgical pencil 100 when sheath 240 of sheath system 200 is in the deployed and/or extended condition. In this manner, accidental and/or inadvertent incidents of pricking are reduced and/or eliminated.

Initially, in order to expose distal end 120*a* of electrocautery blade 120, if sheath system 200 is in a first or deployed condition, wherein sheath 240 at least completely covers distal end 120*a* of electrocautery blade 120 as seen in FIGS. 3 and 5, hub 220 is rotated in a first direction about the longitudinal "X" axis, as indicated by arrow "A" of FIGS. 3 and 5. Since stub 248 of collar 210 is slidingly located in elongate slot 248 of collar 210, upon rotation of hub 220, in the direction of arrow "A", helical groove 226 of hub 220 engages nubs 246 and causes sheath 240 to withdraw or retract (i.e., move in a proximal direction as indicated by arrow "B" in FIGS. 3 and 5). With sheath 240 of sheath system 200 in a withdrawn or retracted condition, the user may operate electrosurgical pencil 100 in a standard or normal fashion.

Following use of electrosurgical pencil 100, sheath 240 of sheath system 200 is deployed in order to once again cover distal end 120*a* of electrocautery blade 120, in order to store electrosurgical pencil 100, to replace electrocautery blade 120 and/or to discard electrocautery blade 120.

In particular, if sheath system 200 is in a second or retracted condition, wherein sheath 240 at least partially uncovers distal end 120*a* of electrocautery blade 120 as seen in FIGS. 4 and 6, in order to recover distal end 120*a* of electrocautery blade 120, hub 220 is rotated in a second or opposite direction about the longitudinal "X" axis, as indicated by arrow "C" of FIGS. 4 and 6. Since stub 248 of collar 210 is slidingly located in elongate slot 248 of collar 210, upon rotation of hub 220, in the direction of arrow "C", helical groove 226 of hub 220 engages nubs 246 and causes sheath 240 to extend (i.e., move in a distal direction as indicated by arrow "D" in FIGS. 4 and 6). With sheath 240 of sheath system 200 in an extended condition, the user may remove electrocautery blade 120 and discard the same with the increased assurance that they will not be stuck or pricked by distal end 120*a* of electrocautery blade 120.

Helical groove 226 formed in body portion 222 of hub 220 may include a notch or catch-point (not shown) formed near a distal end thereof. The notch formed in helical groove 226 is configured and dimensioned to selectively receive a nub 246 of collar 210 when sheath 240 is in the fully deployed and/or extended condition. The notch formed in helical groove 226 desirably functions to prevent and/or reduce the likelihood of sheath 240 from sliding back (i.e., moving in a proximal direction) as a result of a force applied, in a proximal direction, to the distal end thereof.

In a further embodiment, hub 220 may include a ratchet or other anti-rotation feature (not shown) which functions to prevent sheath 240 from accidentally or unwantingly sliding proximally thereby exposing distal end 120*a* of electrocautery blade 120. This anti-rotation feature may only be disengageable when electrocautery blade 120 is connected to the distal end of housing 102 of electrosurgical pencil 100. The components of the anti-rotation feature desirably remain with electrocautery blade 120 when electrocautery blade 120 is removed from electrosurgical pencil 100 to provide continued safe handling of electrocautery blade 120.

In one embodiment, the anti-rotation feature is a flexible pawl (not shown) protruding inwardly from the inner surface of body portion 222 of hub 220 and inter-engaging a toothed ring (not shown) in electrocautery blade 120 or collar 210. In use, it is envisioned that when the distal end of housing 102 of electrosurgical pencil 100 enters the proximal end of lumen 228 of body portion 222 of hub 220, housing 102 of electrosurgical pencil lifts the pawl and disengages the pawl from the toothed ring, allowing hub 220 to rotate.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments.

Those skilled in the art will envision other modifications within the scope and spirit of the claims appended hereto.

What is claimed is:

1. An electrosurgical system, comprising:
an electrosurgical device including a housing having a longitudinal axis defined therethrough;
an electrocautery blade assembly configured for selective, removable connection to the electrosurgical device, the electrocautery blade assembly including an electrocautery blade including a proximal end supportable in the housing of the electrosurgical device and a distal end extending distally from the housing;
a sheath system, including:
a hub including a body portion defining a lumen therethrough;
a sheath translatably associated with the hub and including a body portion defining a lumen therethrough; and
a collar configured to support the electrocautery blade therein,
wherein a central axis of the collar, a central axis of the lumen of the hub, a central axis of the lumen of the sheath, and a central axis of the electrocautery blade are axially aligned with each other and the longitudinal axis of the housing such that rotation of the hub results in axial movement of the sheath to expose or cover the distal end of the electrocautery blade.

2. The electrosurgical system according to claim 1, wherein each of the distal end and the proximal end of the electrocautery blade extends from a respective distal and proximal end of the collar.

3. The electrosurgical system according to claim 2, wherein at least a portion of the collar is rotatably supported in the body portion of the hub, and wherein a portion of the collar is disposed in the lumen of the sheath.

4. The electrosurgical system according to claim 1, wherein the proximal end of the collar is at least partially receivable in the housing of the electrocautery device.

5. The electrosurgical system according to claim 1, wherein the body portion of the hub includes at least one helical groove formed in an inner surface thereof.

6. The electrosurgical system according to claim 5, wherein the body portion of the sheath includes at least one nub extending from an outer surface thereof.

7. The electrosurgical system according to claim 6, wherein the nub is configured to slidably engage the groove of the hub.

8. The electrosurgical system according to claim 7, wherein as the hub is rotated the nub of the sheath rides along the helical groove of the hub to translate the sheath in one of a distal and proximal direction.

9. The electrosurgical system according to claim 1, wherein the collar includes an annular flange extending from an outer surface thereof, and wherein the hub includes an annular groove formed in an inner surface of the body portion, the annular groove of the hub configured to slidably receive the annular flange of the collar.

10. The electrosurgical system according to claim 1, wherein the body portion of the sheath includes an elongated slot formed therein, and wherein the collar includes a stub extending from the outer surface thereof, wherein the stub of the collar is configured to slidably engage the elongated slot formed in the body portion of the sheath.

11. The electrosurgical system according to claim 10, wherein the inter-engagement of the stub of the collar in the elongate slot of the sheath prevents rotation of the sheath as the hub is rotated.

12. The electrosurgical system according to claim 11, wherein at least a portion of each of the hub and the sheath is fabricated from non-conductive materials.

13. The electrosurgical system according to claim 1, wherein rotation of the hub in a first direction results in axial movement of the sheath in a first direction to expose the distal end of the electrocautery blade and rotation of the hub in a second direction results in axial movement of the sheath in a second direction to cover the distal end of the electrocautery blade.

14. A sheath system configured to selectively cover an electrocautery blade adapted to connect to an electrosurgical device, the sheath system comprising:
a hub including a body portion defining a lumen therethrough;
a sheath translatably associated with the hub and including a body portion defining a lumen therethrough; and
a collar configured to support the electrocautery blade therein,
wherein a central axis of the collar, a central axis of the lumen of the hub, a central axis of the lumen of the sheath and a central axis of the electrocautery blade are adapted to be axially aligned with each other and adapted to be aligned with a longitudinal axis of a housing of the electrosurgical device when the electrocautery blade is connected to the electrosurgical device such that rotation of the hub results in axial movement of the sheath to one of expose and cover the distal end of the electrocautery blade.

15. The sheath system according to claim 14, wherein the collar includes a proximal end adapted to have a proximal end of the electrocautery blade extending therefrom and a distal end adapted to have a distal end of the electrocautery blade extending therefrom.

16. The sheath system according to claim 14, wherein at least a portion of the collar is rotatably supported in the body portion of the hub, and wherein a portion of the collar is disposed in the lumen of the sheath.

17. The sheath system according to claim 14, wherein the proximal end of the collar is at least partially receivable in the housing of the electrocautery device.

18. The sheath system according to claim 14, wherein the body portion of the hub includes at least one helical groove formed in an inner surface thereof, wherein the body portion of the sheath includes at least one nub extending from an outer surface thereof.

19. The sheath system according to claim 18, wherein the nub is configured to slidably engage the groove of the hub.

20. The sheath system according to claim 19, wherein as the hub is rotated the nub of the sheath rides along the helical groove of the hub to translate the sheath in one of a distal and proximal direction.

\* \* \* \* \*